(12) United States Patent
Dvir et al.

(10) Patent No.: US 12,221,621 B2
(45) Date of Patent: Feb. 11, 2025

(54) SUPPORT MEDIUM FOR 3D PRINTING OF BIOMATERIALS

(71) Applicant: Ramot at Tel-Aviv University Ltd., Tel-Aviv (IL)

(72) Inventors: Tal Dvir, Tel-Aviv (IL); Assaf Shapira, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 950 days.

(21) Appl. No.: 17/059,236

(22) PCT Filed: Jun. 4, 2019

(86) PCT No.: PCT/IL2019/050635
§ 371 (c)(1),
(2) Date: Nov. 26, 2020

(87) PCT Pub. No.: WO2019/234738
PCT Pub. Date: Dec. 12, 2019

(65) Prior Publication Data
US 2021/0207083 A1   Jul. 8, 2021

Related U.S. Application Data

(60) Provisional application No. 62/679,996, filed on Jun. 4, 2018.

(51) Int. Cl.
| | | |
|---|---|---|
| *C12N 5/00* | (2006.01) | |
| *A61L 27/26* | (2006.01) | |
| *A61L 27/36* | (2006.01) | |
| *A61L 27/52* | (2006.01) | |
| *B33Y 70/10* | (2020.01) | |
| *B33Y 80/00* | (2015.01) | |

(52) U.S. Cl.
CPC ............ *C12N 5/0075* (2013.01); *A61L 27/26* (2013.01); *A61L 27/3637* (2013.01); *A61L 27/52* (2013.01); *B33Y 70/10* (2020.01); *B33Y 80/00* (2014.12); *C12N 2513/00* (2013.01); *C12N 2533/74* (2013.01)

(58) Field of Classification Search
CPC ....... A61K 9/5036; A61K 9/5161; A61K 8/19
See application file for complete search history.

(56) References Cited

U.S. PATENT DOCUMENTS

| | | |
|---|---|---|
| 2008/0044900 A1 | 2/2008 | Mooney et al. |
| 2008/0069801 A1 | 3/2008 | Lee et al. |
| 2011/0177590 A1 | 7/2011 | Clyne et al. |
| 2015/0057786 A1 | 2/2015 | Murphy et al. |
| 2017/0042820 A1* | 2/2017 | Lebo ................. A61K 9/2054 |

FOREIGN PATENT DOCUMENTS

| | | |
|---|---|---|
| RO | 128708 | 8/2013 |
| WO | WO 2015/017421 | 2/2015 |
| WO | WO-2017177265 A1 * | 10/2017 ............ A61K 38/09 |
| WO | WO 2019/234738 | 12/2019 |
| WO | WO 2024/069629 | 4/2024 |

OTHER PUBLICATIONS

Sugiura et al (Biomaterials, 2005, vol. 26, pp. 3327-3331) (Year: 2005).*
Pongjanyakul et al (International Journal of Pharmaceutics, 2007, vol. 331, pp. 61-71) (Year: 2007).*
Supplementary European Search Report and the European Search Opinion Dated Feb. 17, 2022 From the European Patent Office Re. Application No. 19814062.6. (11 Pages).
Fang et al. "Rehydration of Dried Alginate Gel Beads: Effect of the Presence of Gelatin and Gum Arabic", Carbohydrate Polymers, XP055888676, 86(3): 1145-1150, Available Online Jun. 11, 2011.
Noor et al. "3D Printing of Personalized Thick and Perfusable Cardiac Patches and Hearts", Advanced Science, XP055888280, 6(11): 1900344-1-1900344-10, Apr. 15, 2019.
Shapira et al. "Transparent Support Media for High Resolution 3D Printing of Volumetric Cell-Containing ECM Structures", Biomedical Materials, XP020354674, 15(4): 45018-1-45018-16, Jun. 29, 2020.
Tan et al. "Concentric Bioprinting of Alginate-Based Tubular Constructs Using Multi-Nozzle Extrusion-Based Technique", International Journal of Bioprinting, XP055888375, 1(1): 49-56, Published Online Jul. 2, 2015.
Communication Pursuant to Article 94(3) EPC Dated Feb. 21, 2023 From the European Patent Office Re. Application No. 19814062.6 (7 Pages).
International Search Report and the Written Opinion Dated Aug. 29, 2019 From the International Searching Authority Re. Application No. PCT/IL2019/050635. (14 Pages).
Aarstad et al. "Mechanical Properties of Composite Hydrogels of Alginate and Cellulose Nanofibrils", Polymers, 9(8): 378-1-378-19, Aug. 19, 2017.
Bhattacharjee et al. "Writing in the Granular Gel Medium", Science Advances, 1(8): e1500655-1-e1500655-6, Sep. 25, 2015.
He et al. "Research on the Printability of Hydrogels in 3D Bioprinting", Scientific Reports, 6: 29977-1-29977-13, Jul. 20, 2016.
Hinton et al. "3D Printing PDMS Elastomer in A Hydrophilic Support Bath via Freeform Reversible Embedding", ACS Biomaterials Science & Engineering, 2(10): 1781-1786, May 4, 2016.
Hinton et al. "Three-Dimensional Printing of Complex Biological Structures by Freeform Reversible Embedding of Suspended Hydrogels", Science Advances, 1(9): e1500758-1-e1500758-10, Oct. 23, 2015.
Kuo et al. "Ionically Crosslinked Alginate Hydrogels as Scaffolds for Tissue Engineering: Part I. Structure, Gelation Rate and Mechanical Properties", Biomaterials, 22(6): 511-521, Mar. 15, 2001.

(Continued)

*Primary Examiner* — Mark V Stevens

(57) ABSTRACT

Provided herein is a see-through transparent, stable, safe and (bio)degradable hydrogel-based particulate support medium, made of calcium alginate particles. The calcium alginate particles, or hybrid hydrogel particles, are characterized by a substantially homogeneous average particle size that ranges from 0.1 micrometer to 5 micrometer.

20 Claims, 10 Drawing Sheets

(56) References Cited

OTHER PUBLICATIONS

O'Bryan et al. "Self-Assembled Micro-Organogels for 3D Printing Silicone Structures", Science Advances, 3(5): e1602800-1-e1602800-8, May 10, 2017.
Stumberger et al. "Freeform Perfusable Microfluidics Embedded in Hydrogel Matrices", Materials, 11(12): 2529-1-2529-8, Published Online Dec. 12, 2018.
Communication Pursuant to Article 94(3) EPC Dated Dec. 8, 2023 From the European Patent Office Re. Application No. 19814062.6 (8 Pages).
International Search Report and the Written Opinion Dated Dec. 24, 2023 From the International Searching Authority Re. Application No. PCT/IL2023/051038. (12 Pages).
Andersen et al. "3D Cell Culture in Alginate Hydrogels", Microarrays, 4(2): 133-161, Mar. 24, 2015.
Hazur et al. "Improving Alginate Printability for Biofabrication: Establishment of a Universal and Homogeneous Pre-Crosslinking Technique", Biofabrication, 12(4): 045004-1-045004-17, Jul. 9, 2020.

* cited by examiner

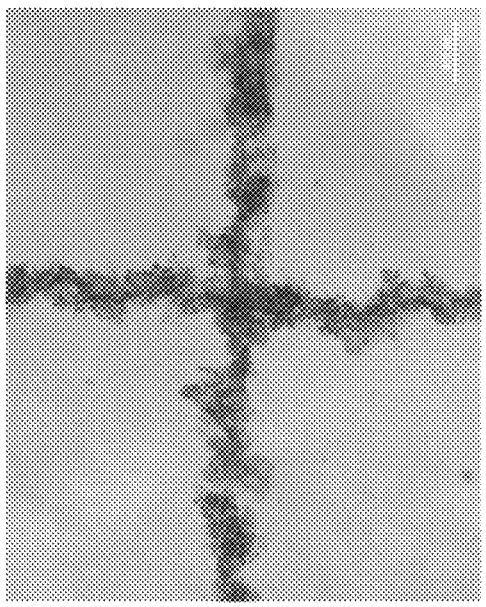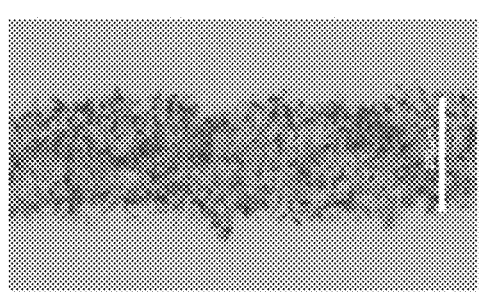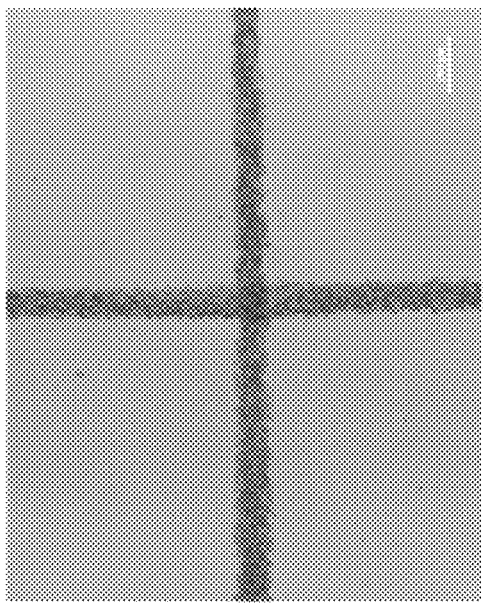
FIG. 5A  FIG. 5C
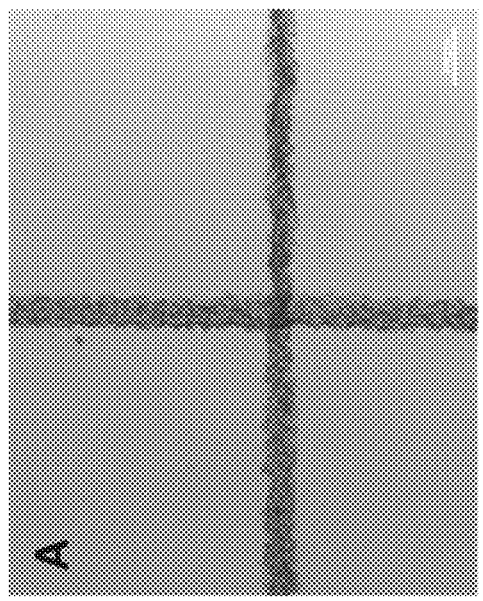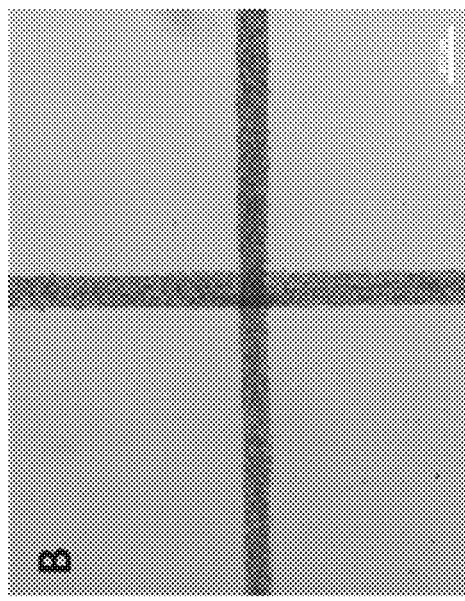
FIG. 5B  FIG. 5D

SUPPORT MEDIUM FOR 3D PRINTING OF BIOMATERIALS

RELATED APPLICATIONS

This application is a National Phase of PCT Patent Application No. PCT/IL2019/050635 having International filing date of Jun. 4, 2019, which claims the benefit of priority under 35 USC § 119 (e) of U.S. Provisional Patent Application No. 62/679,996 filed on Jun. 4, 2018. The contents of the above applications are all incorporated by reference as if fully set forth herein in their entirety.

FIELD AND BACKGROUND OF THE INVENTION

The present invention, in some embodiments thereof, relates to 3D printing of biomaterials, and more particularly, but not exclusively, to a support medium for printing biomaterials based on biocompatible hydrogel particles.

Tissue engineering is a field of science that integrates knowledge from biology, materials sciences, engineering and medicine to develop artificial, functional tissue constructs to replace or support defected tissues. Rather than simply introducing cells into the diseased area to repopulate the injured tissue and restore function, tissue engineering involves the seeding of cells in or onto 3-dimensional (3D) biomaterials prior to transplantation. These materials serve as temporary scaffolds supporting the cells and promoting their reorganization to a functional tissue. Following implantation and full integration in the host, the scaffold degrades, leaving a functional tissue patch on the defected organ. In recent years it has been recognized that effective organization of cells into tissues with morphological and physiological features resembling those in vivo requires a 3D scaffold that precisely mimic the biochemical, structural and mechanical properties of the natural tissue's extracellular matrix (ECM).

Thus, researchers have initially focused on developing materials and technological tools to recapitulate aspects of this specialized microenvironment. While synthetic scaffolds made of biocompatible materials can be fabricated to closely mimic the ECM structure, they still lack much of the fine, complex architecture and biochemical cues that can be found in the native ECM. Contrary, ECM and ECM derived materials can be processed, manipulated and fabricated to create a 3D scaffold that reliably recapitulate the natural cell microenvironment.

One of the most promising methodologies for fabrication of complex, artificial tissue patches is the emerging "bottom-up" or "modular" approach. This method is based on the generation of "modules", namely microscale tissue building blocks that incorporate a complex artificial micro and nano architecture that resemble to that of a native tissue. The modules can be fabricated by using various methods such as cell printing, self-assembled cell aggregates, generation of cell sheets and fabrication of cell-laden hydrogels. These building blocks are than assembled to form a large tissue construct using methods like random packing, stacking of layers and 3D bioprinting.

Three-dimensional (3D) printing is a technology that allows bottom-up construction of complex structures. The boundaries of the printed model are defined by a computer-aided design (CAD) software and accordingly the printer deposits the material in a layer by layer manner. Recent advances in the field have enabled utilization of various printing technologies for delivering living cells with materials. Although in its infancy, one of the promising technologies to print tissues is by microextrusion. Compared to inkjet and laser-assisted printing, which deposit dissociated liquid droplets, extrusion printers use robotically controlled extrusion heads to deposit continues strands of materials in which cells can be incorporated. Up to date such printers have been used to print aortic valves and branched vascular trees. However, printing complex tissues such as the myocardium, which consists of various cell types (cardiac fibroblasts and myocytes) together with a dense vasculature, remained a challenge. One of the main reasons for that is the relatively inferior physical properties of biomaterials such as natural, ECM derived substances that are being used as biocompatible and biodegradable "bio-inks" for the printing process. In contrast to synthetic polymers, fabrication of thick, multilayered complex structures with the abovementioned substances results in an unstable structure with low shape fidelity when executed using conventional microextrusion 3D printing methods. A suitable temporary support that holds the extruded material and stabilizes the delicate printed structure until it is fully cured is a possible solution to this problem.

WO 2015/017421 discloses structure material that comprises a fluid that transitions to a solid or semi-solid state after deposition of the structure material, wherein the support material comprises material comprises a gel material, a hydrogel material, μm-sized particulates and/or a thermo-reversible material. WO 2015/017421 appears to disclose a method for fabricating a structure such as a biological tissue or a tissue engineering scaffold using 3D printing, where the printing method comprises a support bath within which the tissue scaffold is fabricated and which provides divalent cations for crosslinking the printed material. Further, use of a cross-linker concentration in a method for producing rapid prototyping is discussed in EP1517778B; while DE102012100859A discloses a method for producing and printing a 3D structure containing living cells, which may comprise of printing in a high density liquid.

WO 2016/040095 discloses support matrix for 3D printing, comprising a graphene aerogel or a gelled ionic liquid, wherein the gelled ionic liquid comprises an ionic liquid gelled with fumed silica, precipitated silica, chalk, carbon black, paraffin composition, silicone oil, or any combination thereof.

U.S. Patent Application Publication No. 20180057682 discloses an organic microgel system as support material for 3D printing of soft materials such as silicone and methods for manufacturing and using the organic microgel system. According to this document, the organic microgel system comprises a plurality of microgel particles formed by blending a di-block copolymer and a tri-block copolymer in an organic solvent, thereby forming an organic microgel system for high precision 3D printing of silicone objects with complex shapes.

Additional background art includes WO 2017/081040, WO 2014/194180, WO 2014/194180, US2015057786, EP 1517778 and DE 102012100859, and Aarstad et al., *Polymers*, 2017; Bhattacharjee et al., *Sci. Adv.*, 2015; He et al., *Sci. Reports.*, 2016; Hinton et al., *ACS Biomater. Sci. Eng.*, 2016; Hinton et al., *Sci. Adv.*, 2015; Kuo et al., *Biomaterials*, 2001; and O'Bryan et al., *Sci. Adv.*, 2017.

SUMMARY OF THE INVENTION

En route toward fulfilling the nisus of fully personalized engineering of human organs, the present invention provides the means to achieve personalized engineered cardiac patches. The method provided herein involves a biopsy of omental tissue that is taken from a patient, where after the cellular and a-cellular materials are separated. While the cells are reprogrammed to become pluripotent stem cells, the ECM is processed into a personalized, temperature-sensitive hydrogel that can be used as a "bioink" for 3D printing. Following mixture of the cells and the hydrogel to generate cellularized bioinks, the printed cells efficiently differentiate to cardiac cells to create patient-specific, immunocompatible cardiac patches. However, printing of these cardiac patches is limited to relatively thin structures with simple geometry, resulting from the delicate nature of the ECM-derived bioinks that tends to collapse in its uncured state. Thus, a printing strategy has been developed and disclosed herein, aiming to maintain the shape of the printout until the bioinks are fully cured. This strategy can be specifically tailored to support the unique features of the omentum-derived bioink formulation.

To this end, disclosed herein is a unique microparticulate support medium that fits the printing of the personalized hydrogel. The prior art teaches a semi-transparent support medium composed of gelatin microparticles, which allowed to print embryonic heart structure that did not contained cells. Such strategy could support free-form printing of structures composed of a variety of bioinks; however, as the extraction procedure of the support is based on quick melting of the gelatin microparticles at 37° C., such strategy would not allow long-term support until the personalized hydrogel is fully cured. Other strategies include the use of synthetic, transparent granular support for printing cellular structures; however, in this case the integrity of delicate structures and viability of sensitive cells can be jeopardized by the mechanical removal of the support medium.

In contrast to the formulations that have been previously developed by others, the support medium presented herein provides a unique combination of features, all of which are essential for efficient and accurate 3D printing with omentum-derived hydrogels, in particular, and with ECM-derived bioinks, in general. The support media is both transparent, biocompatible (and made of non-animal origin materials), cell-friendly, allows free-form printing and curing in a wide range of temperatures, and extraction by a controllable, non-mechanical delicate process.

Hence, according to an aspect of some embodiments of the present invention there is provided a hydrogel-based particulate support medium, comprising a plurality of calcium alginate hydrogel particles have an average size that ranges from 0.1 µM to 5 µM.

According to some embodiments of the invention, the plurality of calcium alginate hydrogel particles is substantially transparent to visible light.

According to some embodiments of the invention, the support medium presented herein is characterized by a particle size distribution of less than 20% RSD.

According to some embodiments of the invention, the support medium further includes a soluble polymer (namely the support medium is a hybrid hydrogel).

According to some embodiments of the invention, the soluble polymer is xanthan gum.

According to some embodiments of the invention, the concentration of the xanthan gum ranges 0.05%-0.5% w/w or w/v.

According to some embodiments of the invention, the support medium provided herein is in a form of an aqueous slurry.

According to an aspect of some embodiments of the present invention there is provided a selling unit which includes the support medium presented herein.

According to some embodiments of the invention, the support medium is sterile and/or detoxified.

According to some embodiments of the invention, the support medium is ready for use without further dilution.

According to some embodiments of the invention, the support medium is in the form of a drained slurry.

According to some embodiments of the invention, the selling unit is packaged in a packaging material and identified in print on or in the packaging material, for use as a support medium in 3D printing process and/or printer.

According to another aspect of some embodiments of the present invention there is provided a process of preparing the support medium provided herewith; the process is carried out by:

pulverizing a hybrid hydrogel to thereby obtain hybrid hydrogel particles; and washing the hybrid hydrogel particles, thereby obtaining the hydrogel-based particulate support medium, wherein the hybrid hydrogel includes calcium ions, alginate and an additional soluble polymer that is not alginate.

According to some embodiments of the invention, the process further includes, prior to the pulverizing step, co-jellifying alginate and the additional soluble polymer using a source of calcium ions, thereby obtaining the hybrid hydrogel.

According to some embodiments of the invention, the process further includes, prior to the pulverizing step, jellifying alginate using a source of calcium ions to thereby obtain an alginate hydrogel, and thereafter contacting the alginate hydrogel with a soluble polymer, thereby obtaining the hybrid hydrogel.

According to some embodiments of the invention, the process further includes jellifying alginate using a source of calcium ions to thereby obtain an alginate hydrogel, and thereafter pulverizing the alginate hydrogel in the presence of soluble polymer, thereby obtaining hybrid hydrogel particles.

According to some embodiments of the invention, the source of calcium ions is an insoluble calcium salt.

According to some embodiments of the invention, the jellifying is effected in the presence of an acidifying agent.

According to some embodiments of the invention, the acidifying agent is glucono delta-lactone (GDL).

According to some embodiments of the invention, the process further includes, subsequent to the washing step, adding a soluble polymer to the hybrid hydrogel particles.

According to some embodiments of the invention, adding the soluble polymer is effected by contacting the hybrid hydrogel particles with an aqueous solution of the soluble polymer at a final concentration of 0.05%-0.5% w/w or w/v.

According to some embodiments of the invention, the process further includes, after contacting the hybrid hydrogel particles with an aqueous solution of the soluble polymer, incubating the hybrid hydrogel particles in the aqueous solution of the soluble polymer followed for a time period of a least 1 minute. In some embodiments, the contacting and/or incubating further includes mixing, and preferably vigorous mixing.

According to some embodiments of the invention, the soluble polymer is xanthan gum.

According to yet another aspect of some embodiments of the present invention, there is provided a 3D printing process, effected in the hydrogel-based particulate support medium presented herein.

According to yet another aspect of some embodiments of the present invention, there is provided a 3D printing process, effected in xanthan gum solution having a concentration that ranges from 0.5 to 5% w/v.

According to some embodiments of the invention, the xanthan gum is sterilized and/or detoxified.

According to yet another aspect of some embodiments of the present invention, there is provided an article of manufacturing, prepared by 3D printing in the support medium presented herein, namely the hydrogel-based particulate support medium according to embodiments of the present invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying images. With specific reference now to the images in detail, it is stressed that the particulars shown are by way of example and for purposes of illustrative discussion of embodiments of the invention. In this regard, the description taken with the images makes apparent to those skilled in the art how embodiments of the invention may be practiced.

In the images:

FIGS. 1A-B presents photographs of two samples of pulverized calcium alginate hydrogels, wherein FIG. 1A shows a pulverized sample of calcium alginate hydrogel prepared without xanthan gum, and FIG. 1B shows a pulverized sample of calcium alginate hydrogel prepared with xanthan gum (scale bar=50 μm)

FIGS. 5A-D demonstrate the difference in accuracy of printing in a non-supplemented particulate support medium or in support medium supplemented with final concentration of 0.05% (w/v) xanthan gum following the washing steps, wherein FIG. 5A shows a 3D element printed 3 minutes after vortexing a support medium without xanthan gum, FIG. 5B shows a 3D element printed 3 minutes after vortexing a support medium supplemented with xanthan gum, FIG. 5C shows a 3D element printed 3 hours after vortexing a support medium not supplemented with xanthan gum, and FIG. 5D shows a 3D element printed 3 hours after vortexing a support medium supplemented with xanthan gum;

FIGS. 7A-F present microscopic images of a simple crisscross 2-layered pattern printed in two types of support media, wherein FIGS. 7A-C show the pattern as printed in a particulate alginate support medium supplemented with 0.05% w/v xanthan gum, and FIGS. 7D-F show a similar pattern printed into a support medium consisting of 1% (w/v) xanthan gum in an aqueous cell growth medium.

DESCRIPTION OF SOME SPECIFIC EMBODIMENTS OF THE INVENTION

Figure 1A:
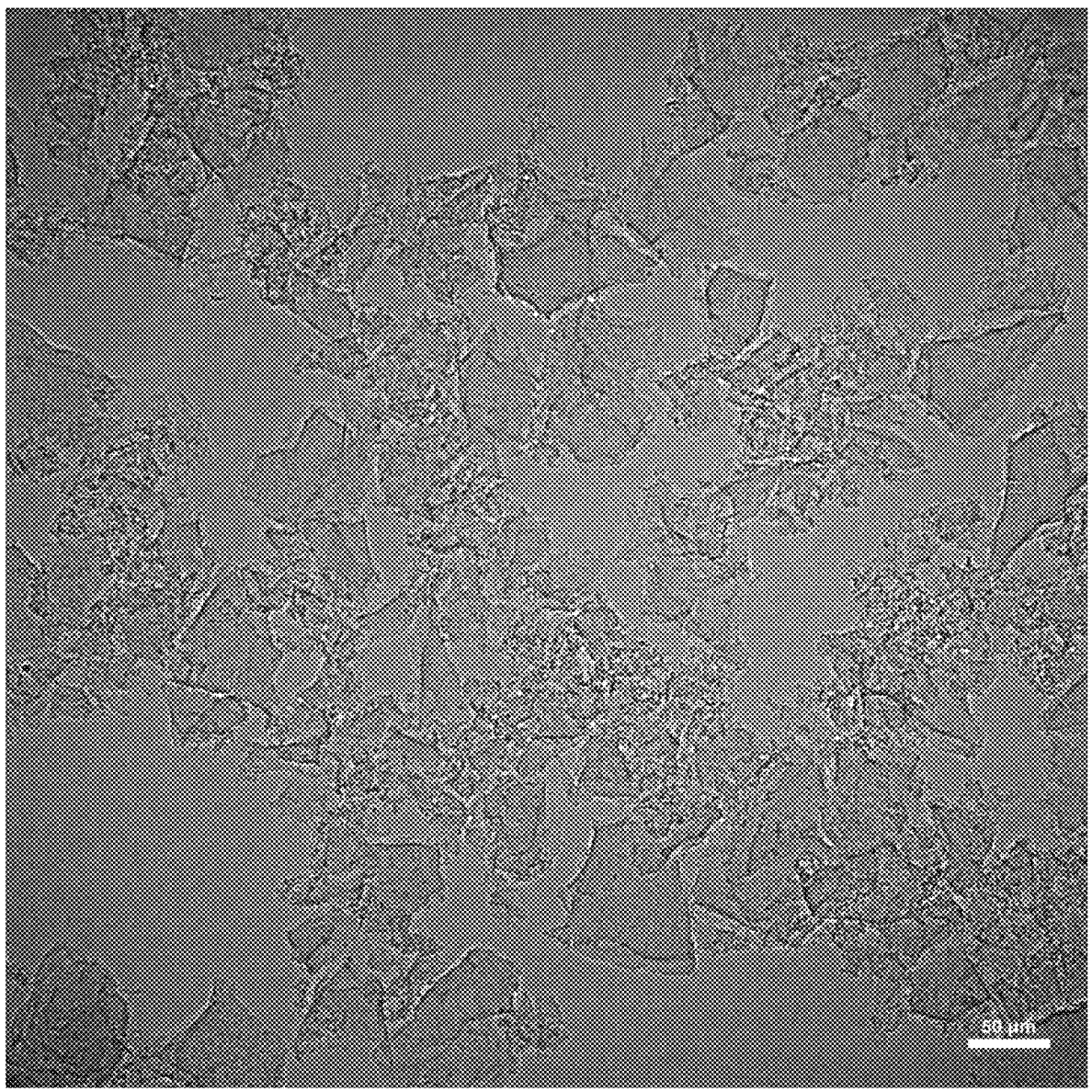

The present invention, in some embodiments thereof, relates to 3D printing of biomaterials, and more particularly, but not exclusively, to a support medium for printing biomaterials based on biocompatible hydrogel particles.

The principles and operation of the present invention may be better understood with reference to the figures and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present invention provides a unique support medium that allows stable 3D printing of complex, multilayered structures composed, inter alia, of biomaterials, such as processed ECM and/or ECM derived substances at high resolution, using a fabrication method based on fused-deposition modeling within the unique support medium. At the basis of the present invention is a special formulation and preparation of a hybrid hydrogel composed of calcium alginate (the structural component of the hydrogel) and xanthan gum (a washable additive used to destabilize the calcium alginate gel, making it amenable for further processing such as crushing and grinding, as well as to facilitate and preserve the homogeneity of the grinded material). In addition, it was found that the presence of a soluble polymer in the support medium, such as xanthan gum, enhances the optical clarity of the support medium and improves printing accuracy and precision. Thus, the role of additives such as xanthan gum, being "washable", has been extended by re-introduction to the medium after the washing steps, so as to become a component in the "final" support medium. In other words, it is optional to preserve the formulation as a "hybrid hydrogel" (e.g., calcium-crosslinked alginate particles supplemented with xanthan gum) in all steps, including in the final step of the process in which the support medium is being generated before using it for printing. The hydrogel is processed into a transparent, μm-sized calcium-alginate uniform and granular support media in which the structure is printed. This granular support media supports the printed biomaterial and preserve its shape during the fabrication process and the following curing phase. When the printed biomaterial is fully cured, the transparent biocompatible, biodegradable, heat stable, non-animal origin support medium can be degraded, releasing a stable, self-supported structure. Of note, this support medium can also be used for printing other curable extruded material, not only biomaterials. Its excellent transparency is especially beneficial in cases when the user needs to inspect the printed construct while fabricated and modify printing parameters accordingly without interrupting the procedure.

As presented hereinabove, the challenges facing the rapidly evolving 3D printing of biomaterial, have been dealt with by various approaches, such as, for example, printing in granular support media composed of gelatin microparticles, as described in WO 2015/017421 and by Hinton et al. (*Science Advances*, 2015). However, these approaches suffer from several major drawbacks. First, the relatively low transparency of the described support media limits real-time monitoring of the printing process. Second, this technology cannot be used to print objects composed of materials that require curing at elevated temperatures in order to achieve stabilized construct conformation, since gelatin is heat-labile and undergoes extensive transformation in its physical properties upon heating (liquefaction), resulting in loss of capability to support the uncured or the not fully cured structure. The heat-lability of gelatin also prevent its use as a pre-heated granulated support media in which the curing of the printed material takes place during the fabrication process. Of note, as gelatin derived from collagen, a major component of the ECM, it can interact adversely with it during fibrillogenesis (when using processed ECM and/or ECM derived substances as printing materials), thus "contaminating" the final structure with the support material. In addition, gelatin is of an animal source, a fact that may rise safety concerns in medical applications. Contrary to these limitations, the presently disclosed support medium is composed of transparent calcium-alginate hydrogel which is heat-stable, inert (do not interact with materials such as processed ECM and/or ECM derived substances) and is of a non-animal origin.

In addition, 3D printing in granular support media composed of Carbopol® (high molecular weight crosslinked polyacrylic acid polymers) microparticles, has been described in Bhattacharjee et al. (*Science Advances*, 2015). However, as Carbopol® is not recognized as a biocompatible and biodegradable product, it is less suitable for tissue engineering and regenerative medicine application. Furthermore, its resolution from the printed construct is complicated and cannot be performed by using mild procedures like chelation and/or enzymatic digestion. Contrary to Carbopol®, the transparent support medium provided herein is made of alginate which is biocompatible, biodegradable and is widely used as a biomaterial for tissue engineering applications. In addition, it can be readily resolved from the printed structure by a mild chemical (chelation) and/or enzymatic treatment.

A Process of Preparing Hydrogel-Based Particulate Support Media:

A unique formulation of calcium alginate-xanthan gum hybrid hydrogel, provided herein, was surprisingly found of being capable of being processed into a calcium alginate hydrogel-based fine and uniform particulate media, highly suitable for 3D-printing support media. The support media provided herein is characterized by advantageous heat and mechanical stability, as well as advantageous see-through transparency. While transparent calcium alginate hydrogels are known in the art, it is the novel combination of alginate and an additional water soluble and biocompatible polymer, such has xanthan gum, at specific range of ratios, which has been found to afford the novel fine particulate hydrogel support medium for 3D printing. The combination of two or more polymers in the formation and/or processing of a hydrogel is referred to herein as a "hybrid hydrogel". Thus, in the context of the present invention, the term "hybrid hydrogel" refers to a hydrogel or a processed hydrogel preparation that comprises at least two types of polymers (at least one of them can form a hydrogel), either by co-jellification or by pre- or in-(pulverizing/grinding) processing introduction or by post-washing introduction/re-introduction a second (or more) polymer into the formed hydrogel network and/or to its surroundings.

Without being bound by any particular theory, it is assumed that the soluble polymer interacts with the crosslinked polymeric network in the hybrid hydrogel in more than one way, regardless of the process by which the two entities are brought in contact and processed. For example, regardless whether the hybrid hydrogel is formed by co-jellification, washing, re-introduction and grinding; or the soluble polymer is introduced into the pre-formed and washed crosslinked polymeric network before, during or after grinding; or a combination of any of the aforementioned or the hydrogel is preformed and only after it formation it is brought in contact with the soluble polymer prior to grinding, the soluble polymer may infiltrate the crosslinked polymeric network, and/or coat the crosslinked polymeric network on accessible surfaces thereof. Without being bound by any particular theory, it has been noted by the inventors that the presence of the two elements in the hybrid hydrogel allows for finer and more uniform grinding of the crosslinked polymeric network, and inhibits the formation of aggregates thereof. The simplistic hypothetic model of how the soluble polymer affects the crosslinked polymeric network (hydrogel) is by integrating inside the hydrogel network and changing the properties of the bulk material. In fact, this is the most intuitive concept of "hybrid hydrogel". However, the effect of the soluble polymer may also be mediated by other forms of molecular behavior. For example, few studies showed that when mixing xanthan gum and alginate molecules, phase separation may occur. In other words, it is possible that the xanthan gum molecules do not interact directly the alginate molecules, in which case the beneficial effect of the xanthan gum in the instant embodiments may be mediated by a phenomenon in which the xanthan gum and alginate molecules repel each other, thus weakening the bulk hydrogel structure when co-jellified with alginate, and/or envelop the generated alginate particles following pulverization, with or without penetrating the hydrogel network. This may prevent the alginate particles from aggregation and also may act like a lubricant to allow the particles to move freely and smoothly over each other, thus achieving superb printing-supporting capability.

Hence, the term "hybrid hydrogel", as used herein, is meant to encompass all forms of possible interactions between the soluble polymer molecules (e.g., xanthan gum) and the crosslinked polymeric network (e.g., calcium alginate hydrogel), be it entangled or mechanically bound/entrapped otherwise, infiltrated therein as a leachable, or as an external coating.

According to an aspect of some embodiments of the present invention, there is provided a process of producing the hydrogel-based particulate support medium provided herein, the process includes pulverizing a hybrid hydrogel, which includes a crosslinked polymer, calcium ions and an additional soluble polymer, to thereby obtain hybrid hydrogel particles, and washing the resulting hybrid hydrogel particles in order to substantially remove the remnants of the additional soluble polymer, which is not part of the crosslinked polymeric network, and any leachables and unreacted starting materials, calcium ions and the like. While washes also remove most of the soluble polymer that has not been entangled in the crosslinked polymeric network, a soluble polymer, such as xanthan gum, is optionally (re)introduced into the hydrogel-based particulate support medium in order to enhance the optical clarity of the support medium and improve printing accuracy and precision.

The hybrid hydrogel, according to some embodiments of the present invention, is prepared by co-jellifying calcium ions, alginate and another soluble and compatible polymer, such as xanthan gum, essentially as described in the Examples section that follows below. Without being bound by any particular theory, it is assumed that the addition of an additional soluble polymer, such as xanthan gum, weakens the structure of the calcium alginate hydrogel, as well as facilitating and preserving the homogeneity of the particulate material following pulverizing; hence, while pulverization and homogenization of a calcium alginate hydrogel typically results in large, bulky and irregular flakes and/or aggregates that constitute an inferior support medium, the calcium alginate-xanthan gum hybrid hydrogel can be processed to afford fine, homogenous calcium alginate hydrogel particles (see, FIGS. 1A-B).

Hybrid hydrogel particles may be generated by means other than pulverizing a pre-formed, co-jellified hybrid hydrogel. That is to say, they may also be generated by grinding/pulverizing pre-jellified pristine calcium alginate hydrogel (the crosslinked polymeric network) in a solution that contains the soluble polymer, thereby introducing the soluble polymer into the pre-formed calcium alginate network and/or to its surroundings to afford a hybrid hydrogel. Alternatively, the crosslinked polymeric network may be exposed to the soluble polymer before or after the grinding/pulverizing step. However, the co-jellified hybrid hydrogels were found to be easier to pulverize, enabling to shorten the time needed to complete the process and avoid the presence of large, non-homogenous particles and aggregates, especially when processing stiff alginate gels.

It is noted herein that other soluble and compatible polymers, such as low-melting agarose, methylcellulose and the likes, may also be used to form a hybrid hydrogel with calcium alginate structure, making it processable by homogenization to afford a particulate hydrogel media. The inventors have found that xanthan gum is a preferred biopolymer for serving as the additional soluble polymer, which gave the best results in terms of particle size, stability, processability of the homogenate and ease of extraction from the particles after pulverization and before use. As discussed hereinabove, xanthan gum is beneficial in the final preparation of the support medium; however, extraction of alginate and xanthan is essential to eventually release the printed structure form the support medium.

Figure 1B:
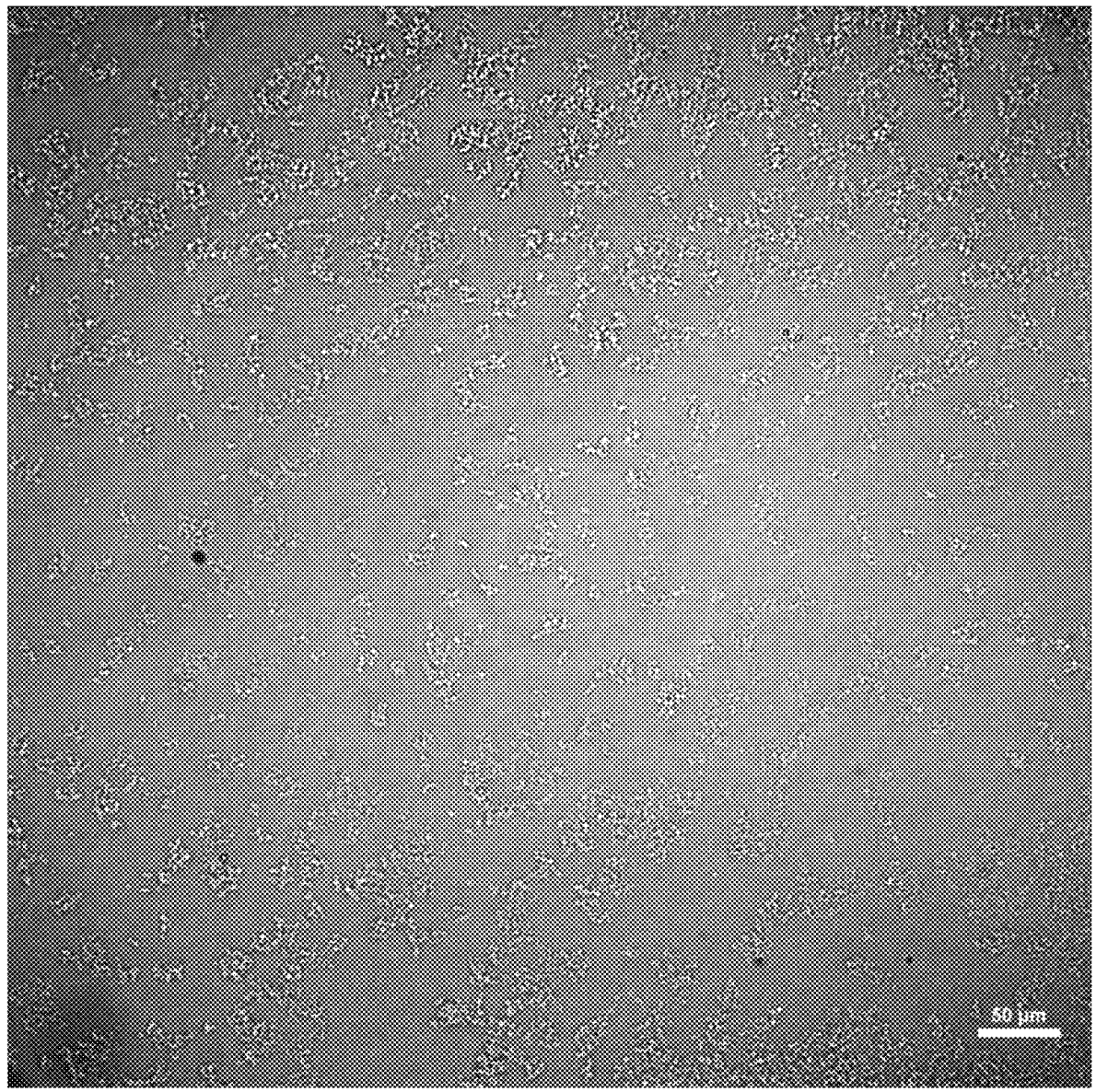

FIGS. 1A-B presents photographs of two samples of pulverized calcium alginate hydrogels, wherein FIG. 1A shows a pulverized sample of calcium alginate hydrogel prepared without xanthan gum, and FIG. 1B shows a pulverized sample of calcium alginate hydrogel prepared with xanthan gum (scale bar=50 μm).

As can be seen in FIGS. 1A-B, calcium alginate hydrogel prepared without xanthan gum breaks into large non-homogeneous flakes and aggregates, while the hybrid hydrogel prepared with xanthan gum, according to some embodiments of the present invention, can be pulverized and homogenized into a fine and homogeneous particulate.

In order to afford highly transparent calcium alginate hydrogel, the jellification process is slowed down. Slowing the jellification process can be achieved, inter alia, by using a water-insoluble source of calcium ions, and further using an acidifying agent that slowly releases calcium ions from the water-insoluble source thereof. In some embodiments, the hybrid hydrogel is prepared using calcium carbonate, which is substantially water-insoluble, with the addition of the acidifying agent glucono delta-lactone (GDL).

Figure 2:
FIG. 2 presents photographs of two samples of pulverized calcium alginate hydrogel support media, showing the transparency of the support media prepared as described herein (left) compared to a preparation of calcium alginate hydrogel composed of microparticles generated by sonication of calcium-alginate in $CaCl_2$ solution (right)

FIG. 2 presents photographs of two samples of pulverized calcium alginate hydrogel support media, showing the transparency of the support media prepared as described herein (left) compared to a preparation of calcium alginate hydrogel composed of microparticles generated by sonication of calcium-alginate in $CaCl_2$ solution (right).

As can be in FIG. 2, the hydrogel particles prepared with an insoluble calcium ion source and an acidifying agent are transparent, while the calcium alginate hydrogel particles made with calcium chloride are opaque.

After homogenization, the suspended hydrogel particles are incubated and washed repeatedly until all remnants of free calcium ions and the additional soluble polymer are washed away.

The washed calcium alginate particles are thereafter collected, i.e., by centrifugation, and re-suspended in water or another aqueous solution for use as support medium for 3D printing.

According to some embodiments of the present invention, some soluble polymers, such as xanthan gum, may be added (or reintroduced) to the support medium for enhancing the optical clarity of the support medium and improving printing accuracy and precision. In such embodiments, after washing, the washed pellet is supplemented with 1% w/v soluble polymer solution, such as xanthan gum solution, to afford a final concentration of 0.05-0.5% w/w or w/v (0.05-0.5 grams of the soluble polymer such as xanthan gum, in a total weight of 100 gr or 100 ml support medium). The mixture is then vigorously mixed, and incubated at room temperature or at 4° C. for several (1-5) days before use. If needed, the viscosity of the support media can be reduced by addition of aqueous solutions containing the same final concentration of xanthan gum as abovementioned.

Hydrogel-Based Particulate Support Media:

According to an aspect of embodiments of the present invention, there is provided a transparent, stable, safe and (bio)degradable hydrogel-based particulate support medium for 3D printing, comprising a plurality of essentially non-aggregated and substantially discrete calcium alginate hydrogel particles having an average size that ranges from 0.1 μM to 5 μM, and a substantially narrow size distribution. The chemical composition of the hydrogel is mostly, or substantially alginate hydrogel crosslinked network, however, some amounts of the soluble polymer may be present in minute amounts, left after repetitive washes, or present in the hydrogel in amounts/concentration that can be controlled by the process of manufacturing the same. Hence, the presence of the soluble polymer in the hydrogel-based particulate support medium may range from essentially none (minute amounts) to any concentration used in the process of making the hydrogel-based particulate support medium.

In the context of some embodiments of the present invention, the plurality of calcium alginate hydrogel particles is referred to as being essentially or substantially devoid of dissociable elements, namely chains and molecules that are not bound to the hydrogel network by direct, indirect or mechanical association. In some embodiments, the calcium alginate hydrogel particles comprising the support medium are substantially devoid of the soluble polymer (e.g., xanthan gum); in some embodiments the calcium alginate hydrogel particles comprises non-leachable (network-bound) chains of the soluble polymer, and regarded as hybrid hydrogel particles; and in some embodiments that the calcium alginate hydrogel particles comprises chains of the soluble polymer introduced or re-introduced into the hydrogel network and/or to its surroundings by soaking after formation of the network (post-jellification), and are also regarded as hybrid hydrogel particles.

The plurality of calcium alginate hydrogel particles, according to embodiments of the present invention, are characterized by being essentially discrete (non-aggregated) and having a relatively narrow size distribution, or a lower coefficient of variation (CV). CV is also known as relative standard deviation (RSD), which is a standardized measure of dispersion of a probability distribution or frequency distribution, and is often expressed in percent. SRD is defined as the ratio of the standard deviation (sigma, σ) to the mean μ). According to some embodiments of the present invention, the plurality of calcium alginate hydrogel particles is characterized by a particle size distribution of less than 5%, less than 10%, less than 20% or less than 25% RSD.

Moreover, as the fine and homogeneous particles of the support medium provided herein, can easily flow throw very fine needles, and can therefore also serve as a sacrificial material in 3D printing of hollow structures.

The high see-through transparency of the support medium to visible light, according to some embodiments of the present invention, allows the printing process to be monitored at real time: the user can inspect the printed construct while fabricated and modify printing parameters accordingly without interrupting the procedure. The high see-through transparency of the media may also allow automatic calibration and monitoring of the printing process by 3D printers equipped with compatible optical sensors. This enables the user to calibrate and tune the printer conveniently and accurately, what results in a refined printout. Finally, the transparency of the support media may enable curing of light-curable printed materials by external illumination. Thus, according to some embodiments of the present invention, the plurality of calcium alginate hydrogel particles is substantially transparent to visible light.

Figure 3:
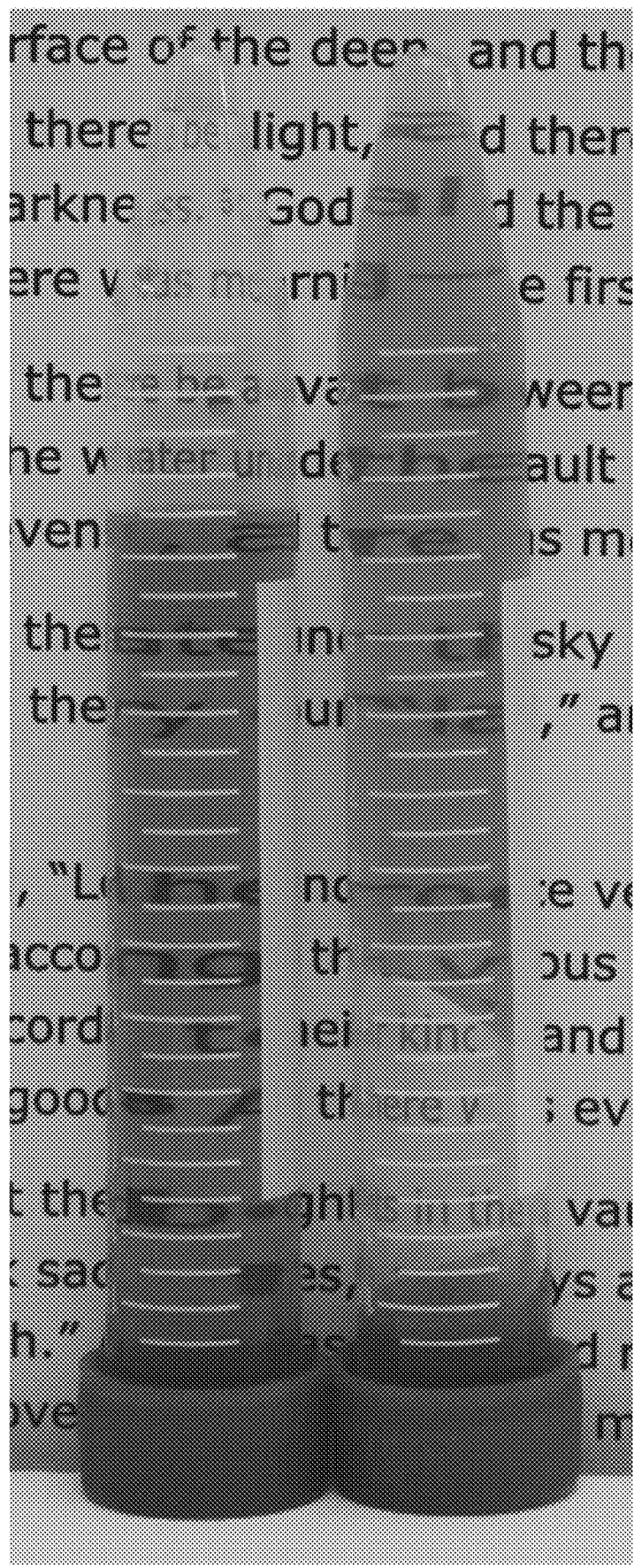
FIG. 3 presents a photograph of two sample vials, comparing the see-through transparency of the support medium provided herein (right), compared to that of a pure cell media (left)

FIG. 3 presents a photograph of two sample vials, comparing the see-through transparency of the support medium provided herein (right), compared to that of a pure cell media (left). As can be seen in FIG. 3, the see-through transparency of both almost identical, demonstrating that the alginate particles of the support medium provided herein, according to embodiments of the present invention, have little effect on the overall clarity of the suspension.

The hydrogel-based particulate support medium provided herein is generally a plurality of hydrogel particles hydrated by an aqueous solution in the form of a slurry or a suspension. The amount of the aqueous solution may vary from essentially no excess thereof (a drained slurry) up to a diluted suspension of the particles at a ratio that allows the printed object to be supported and formed adequately. The preferable amount of dilution is within the routine experimental procedures of a person skilled in the art.

According to some embodiments, the slurry is sterile and free of any toxins or other factors that may adversely affect an article of manufacturing being formed therewithin.

A Selling Unit of the Support Medium:

According to an aspect of some embodiments of the present invention, there is provided a selling unit, comprising the support medium provided herein. The selling unit can be in a form of a sealed and oxygen-proof container that contains an amount of the support medium suitable for a specific printing machine or a specific printing bath size.

According to some embodiments, the selling unit contains a drained support medium, wherein the user is instructed to add an aqueous solution thereto in order to arrive at an adequate dilution of the support medium.

According to some embodiments of the present invention, the selling unit includes a packaging material, and identified in print, or on said packaging material, for use as a support medium in a 3D printing machine and process.

Xanthan Gum as Support Medium:

Xanthan gum pose no risk of toxicity and is generally accepted as safe for human consumption (GRAS). It is fully biocompatible and its water solubility enables simple extraction from the fabricated 3D structure post-printing. Interestingly, the present inventors have surprisingly found that even a pure, non-particulate xanthan gum solution (successfully demonstrated below with 1% w/v solution in cell media) can serve as a support medium for 3D printing, resulting in adequate accuracy and printing resolution.

Xanthan gum aqueous solutions can be used as a transparent, easy to prepare, low-cost, temperature insensitive, non-animal support media for 3D printing of biological and other materials.

Thus, according to an aspect of some embodiments of the present invention, there is provided a process of 3D printing in a support medium, wherein the support medium includes an aqueous solution of xanthan gum at a concentration that ranges from 0.5 to 5% w/v, preferably from 0.8 to 2% w/v, or 1% w/v.

According to some embodiments, the xanthan gum used as a support medium, is sterile, and free of any toxins or otherwise any factors that may adversely affect the printing process or the printed article-of-manufacturing being formed thereby.

A demonstration of the usability of pure xanthan gum hydrogel as support medium for 3D printing and other additive structuring methods is presented in the Example section hereinbelow (see, e.g., FIGS. 7A-F).

3D Printed Article:

High-resolution complex 3D printed objects made of biologic or biocompatible printable materials, can be produced using the hydrogel-based particulate support medium provided herein. The end-users of such technology are patients that will benefit from transplantation of engineered cellular or acellular tissues, organs and/or other types of grafts, as well as the pharma industry that may use the printed structures/tissues/organs for drug screening and testing. For non-medical applications, the end-user of such 3D printed objects is any artisan that benefits from rapid-prototyping/3D printing services and/or products.

Thus, according to an additional aspect of embodiments of the present invention, there is provided an article of manufacturing, afforded by 3D printing the article inside the hydrogel-based particulate support medium described herein.

For clinical/medical applications, the hydrogel-based particulate support medium described herein is useful in high-resolution manufacturing of complex cellular or acellular scaffold articles composed of biomaterials, such as processed ECM or ECM-derived substances, developed for tissue engineering and regenerative medicine, as well as for the purpose of drug screening and testing.

For research applications, the hydrogel-based particulate support medium described herein is useful in high-resolution manufacturing of complex cellular or acellular scaffold articles composed of biomaterials such as processed ECM or ECM-derived substances for tissue engineering and regenerative medicine research, as well as for pharmaceutical research, like screening and testing of drugs.

The hydrogel-based particulate support medium, according to some embodiments of the present invention, is useful in the development of new biomaterials with desirable features, which behavior can be directly monitored during printing by virtue of the high see-through transparency of the support media.

It is expected that during the life of a patent maturing from this application many relevant hydrogel-based particulate support media will be developed and the scope of the term hydrogel-based particulate support media is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrases "substantially devoid of" and/or "essentially devoid of" in the context of a certain substance, refer to a composition that is totally devoid of this substance or includes less than about 5, 1, 0.5 or 0.1 percent of the substance by total weight or volume of the composition. Alternatively, the phrases "substantially devoid of" and/or "essentially devoid of" in the context of a process, a method, a property or a characteristic, refer to a process, a composition, a structure or an article that is totally devoid of a certain process/method step, or a certain property or a certain characteristic, or a process/method wherein the certain process/method step is effected at less than about 5, 1, 0.5 or 0.1 percent compared to a given standard process/method, or property or a characteristic characterized by less than about 5, 1, 0.5 or 0.1 percent of the property or characteristic, compared to a given standard.

The term "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the terms "process" and "method" refer to manners, means, techniques and procedures for accomplishing a given task including, but not limited to, those manners, means, techniques and procedures either known to, or readily developed from known manners, means, techniques and procedures by practitioners of the chemical, material, mechanical, computational and digital arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental and/or calculated support in the following examples.

EXAMPLES

Reference is now made to the following examples, which together with the above descriptions illustrate some embodiments of the invention in a non-limiting fashion.

Example 1

A Hydrogel-Based Printing Support

A proof of concept of some embodiments of the present invention was carried out by forming a hybrid calcium alginate and xanthan gum hydrogel.

Briefly, a hybrid hydrogel, composed of 0.25-0.5% (w/v) sodium alginate (tested with PROTANAL LF 10/60 FT and PROTANAL LF200 FTS, FMC BioPolymer, or KIMIKA ALGIN I-3G by KIMICA corporation), 0.125-0.5% (w/v) xanthan gum (tested with Xantural 180, CP Kelco, Sigma G1253, xanthan gum from *Xanthomonas campestris*), 7.5-15 mM calcium carbonate and 15-30 mM D-(+)-Gluconic acid δ-lactone (GDL) was made by mixing the following ingredients:

25-50% v/v of 1% (w/v) sodium-alginate solution (0.22 μm filtered);

12.5-25% v/v (or centrifuged pellet) of 60 mM suspension of calcium carbonate ($CaCO_3$) in deionized water, sonicated to reduce the size of the calcium-carbonate particles (autoclaved);

0-50% v/v of deionized water (autoclaved or 0.22 µm filtered); and 12.5-50% v/v of 1% (w/v) xanthan gum in 150 mM NaCl solution (autoclaved).

It is noted that a higher percentage of xanthan (up to 0.5%) may be required if using an alginate batch that form stronger gels.

The above ingredients were mixed for at least 30 minutes, and thereafter a fresh GDL solution (0.22 µm filtered) was add to a final concentration of 15-30 mM.

An embodiment of a specific formulation, preferred in terms of printout support capacity and see-through optical clarity is given below:

37.5% (v/v) of 1% (w/v) sodium alginate solution (PROTANAL LF 10/60 FT, FMC biopolymer); 25% (v/v) of 1% (w/v) xanthan gum (Xantural 180, CP Kelco) in 150 mM NaCl solution; 18.75% (v/v) of 60 mM suspension of calcium carbonate, 18.75% (v/v) deionized water, 22.5 mM GDL.

The mixture was vigorously stirred for 3 minutes, after which the stirring speed was lowered to generate a fine turbulence that bends the surface of the liquid. When the bend was no longer visible due to the increase in the viscosity of the reaction mixture, the stirring was stopped and the mixture was incubated uninterrupted, at room temperature, for 24 hours.

The resulting hydrogel was manually broken into chunks to which sterile deionized water at a volume of 4 times the volume of the hydrogel was added to a total volume of 5 times the volume of the hydrogel. The water-suspended hydrogel chunks were thereafter homogenized into fine particles using an electric homogenizer, and the homogenate was incubated over-night at 4° C. to allow dissolution of remaining traces of $CaCO_3$.

The suspension was centrifuged at 15,777 G for 5-20 minutes (depending on the stability of the pellet) at room temperature. Thereafter the pellet was washed 2-5 times with sterile deionized water, added at a volume equal to the discarded supernatant, by repeated centrifugation at 15,777 G for 5-20 minutes at room temperature and re-suspension by vigorous mixing. Lastly, the pellet was washed 1-2 times with cell media, added at a volume equal to the discarded supernatant, by repeated centrifugation at 15,777 G for 5-20 minutes at room temperature and re-suspension by vigorous mixing. Excess calcium ions and xanthan gum are washed away during these washing steps, leaving transparent granular media composed of calcium-alginate particles in the form of a pudding-like pellet.

In some samples, after washing, a soluble polymer, such as xanthan gum, was added to the pudding-like pellets in order to enhance the optical clarity of the support medium and improve printing accuracy and precision.

In the embodiments in which a soluble polymer (xanthan gum) was introduced into the support medium, the procedure further included:

After washing, the washed pellet was supplemented with 1% w/v xanthan gum solution to reach a final concentration of 0.05-0.5% (w/w or w/v; 0.05-0.5 gr xanthan gum in a total weight of 100 gr or 100 ml support medium), vigorously mixed, and incubated at room temperature or at 4 centigrade for 1-5 days before use.

The pudding-like pellet was then transferred to a chamber large enough to contain the printed structure, and manually stirred using a spatula for about 10 seconds. Optionally the pellet can be homogenized using an electric homogenizer and/or vortexed before use.

Example 2

3D Printing into the Hydrogel-Based Printing Support

Printable biologic inks, composed of biomaterials (supplemented or not supplemented with cells) such as processed ECM or ECM-derived substances (or other extrudable materials) were printed within the support media described hereinabove, using a 3D printer equipped with microextrusion tools.

The printing chamber was incubated at 37° C. in order to cure (solidify) the printed structure, considering that incubation at 37° C. is most suitable for processed ECM or ECM-derived substances that incorporate mammalian cells. It is noted herein that incubation at temperatures higher or lower than 37° C. may be used for other ink materials.

The support media was then supplemented with a solution containing a chelating agent, such as citrate and/or EDTA and/or EGTA, and/or depolymerizing enzyme, such as alginate lyase, in order to degrade the alginate particles and release the printed construct.

Example 3

Hybrid Hydrogel Effect

As discussed hereinabove, the support medium, which is composed of specially prepared alginate particles in cell growth medium, may optionally be supplemented after washing with concentrated xanthan gum solution (e.g., 1% w/v in aqueous cell growth medium) to reach a final xanthan gum concentration of 0.05%-0.5% (w/v or w/w) in the support media. It was found that the presence of xanthan gum in the support medium enhances its optical clarity and greatly improves and maintains printing accuracy and precision, especially as time passes following vortexing/stirring/homogenizing of the support medium. It was also found that when supplementing the support medium with low xanthan gum concentrations in the rage of 0.05-0.2% w/v, the mixture requires longer incubation times (e.g., about 72 hours) for the xanthan gum to endow is beneficial effect. This finding was supported by a microscopic analysis, showing that xanthan supplementation improves particles' dispersion and prevent aggregation over time.

Figure 4A:
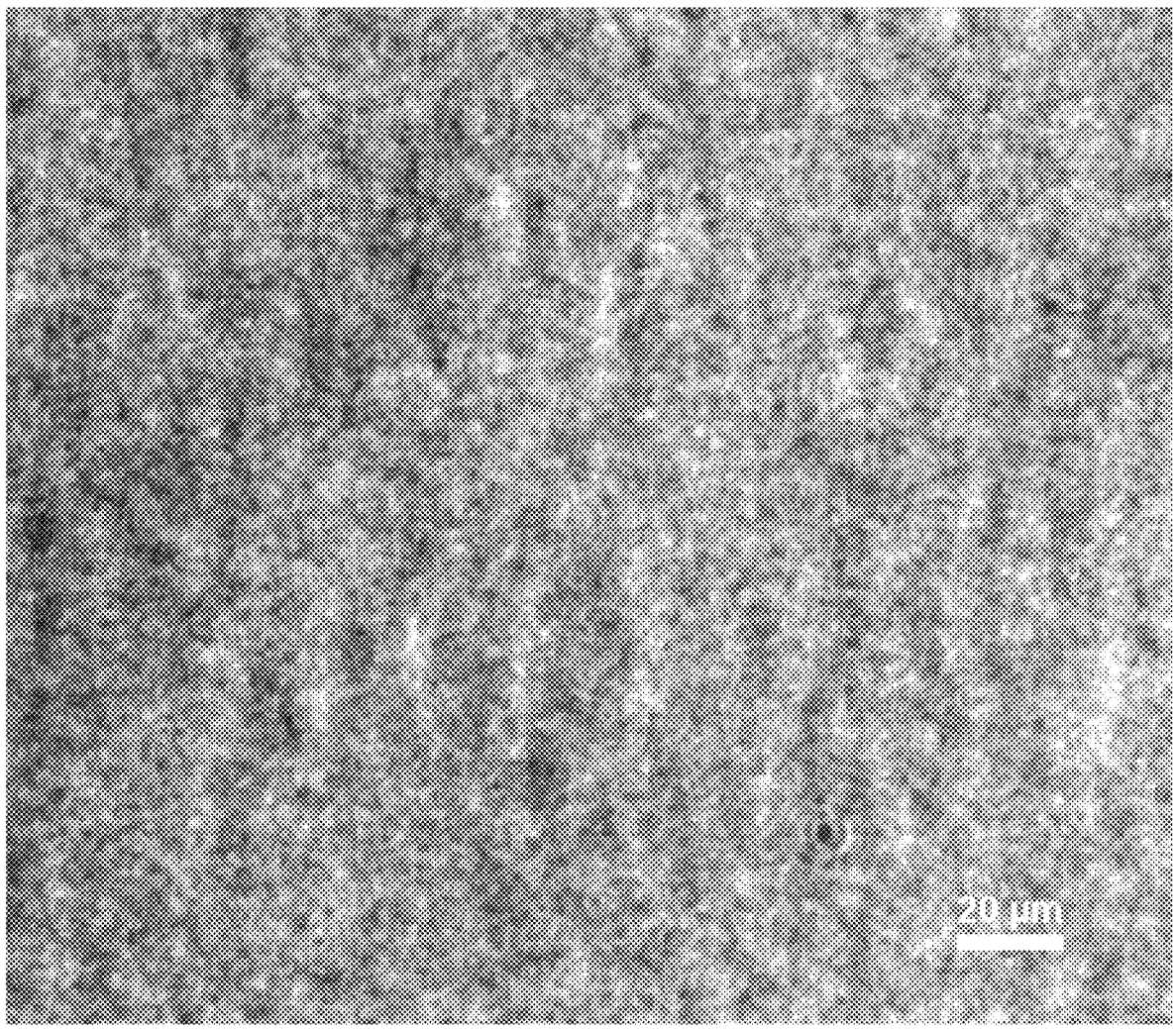
FIGS. 4A-B present microscopic images of alginate particles in a drop of supporting medium without xanthan gum (FIG. 4A) and the same supplemented with final concentration of 0.5% (w/v) xanthan gum after the washing steps (FIG. 4B)
Figure 4B:
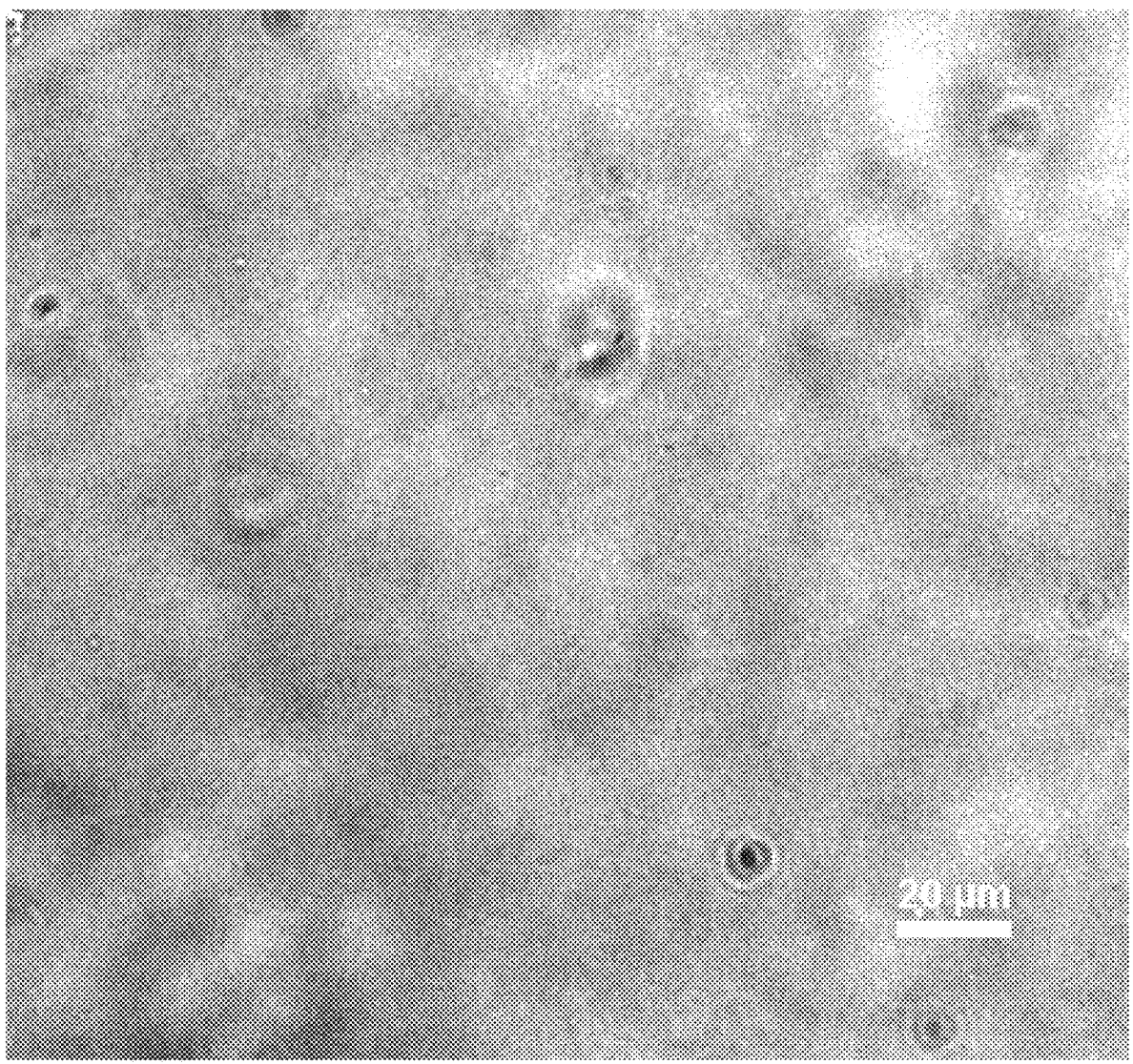

FIGS. 4A-B present microscopic images of alginate particles in a drop of supporting medium without xanthan gum (FIG. 4A) and the same supplemented with final concentration of 0.5% (w/v) xanthan gum after the washing steps (FIG. 4B).

As can be seen in FIGS. 4A-B, the presence of xanthan gum in the support medium enhances its optical clarity.

FIGS. 5A-D demonstrate the difference in accuracy of printing in a non-supplemented particulate support medium or in support medium supplemented with final concentration of 0.05% (w/v) xanthan gum following the washing steps, wherein FIG. 5A shows a 3D element printed 3 minutes after vortexing a support medium without xanthan gum, FIG. 5B shows a 3D element printed 3 minutes after vortexing a support medium supplemented with xanthan gum, FIG. 5C shows a 3D element printed 3 hours after vortexing a support medium not supplemented with xanthan gum, and FIG. 5D shows a 3D element printed 3 hours after vortexing a support medium supplemented with xanthan gum.

As can be seen in FIGS. 5A-D, the presence of xanthan gum in the support medium greatly improved and maintained printing accuracy and precision, especially as time passes following vortexing/stirring/homogenizing of the support medium.

Figure 6A:
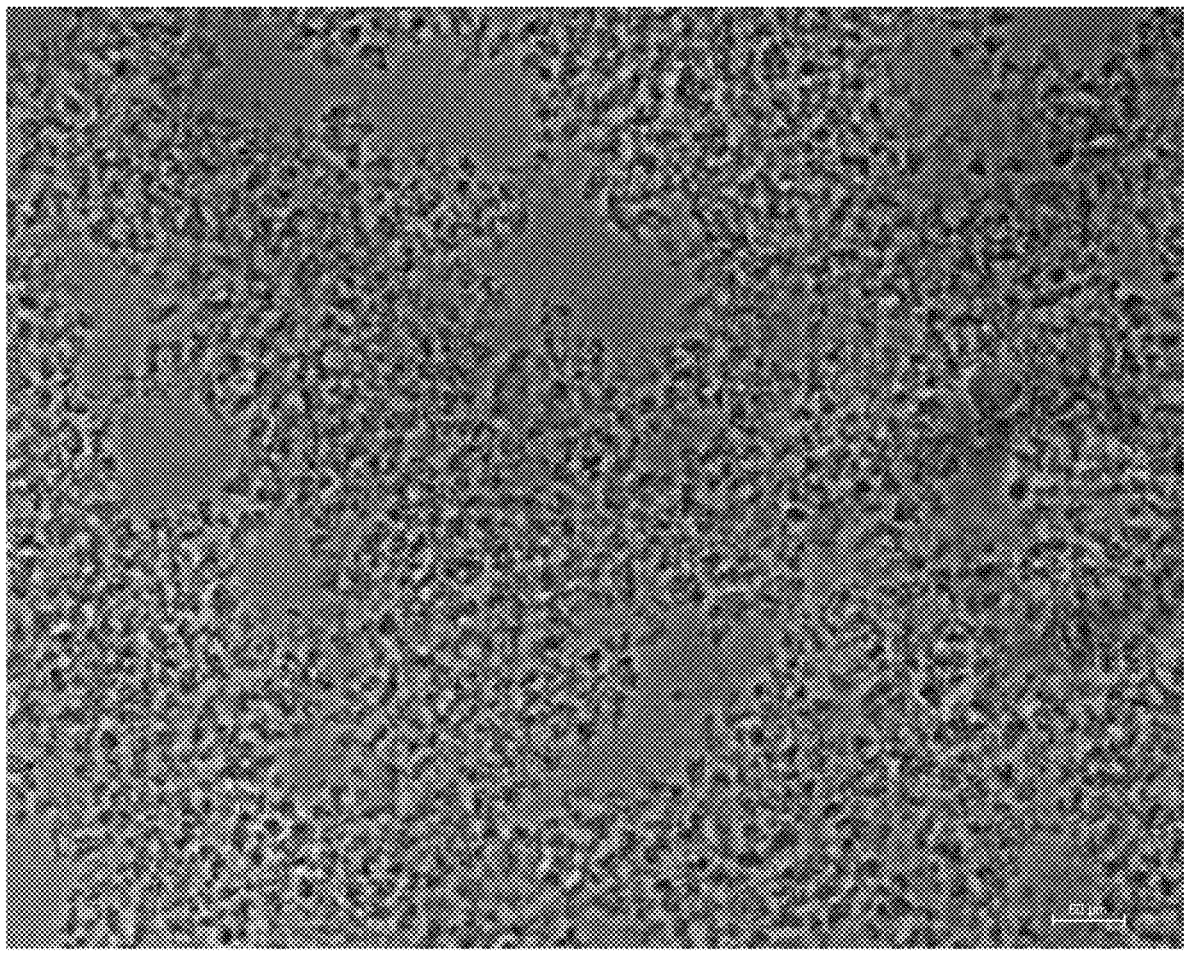
FIGS. 6A-B present microscopic images of alginate particles in a smear of a five-fold diluted supporting medium without xanthan gum (FIG. 6A) or supplemented with final concentration of 0.05% w/v xanthan gum (FIG. 6B), wherein the images were taken 30 minutes after vortexing.
Figure 6B:
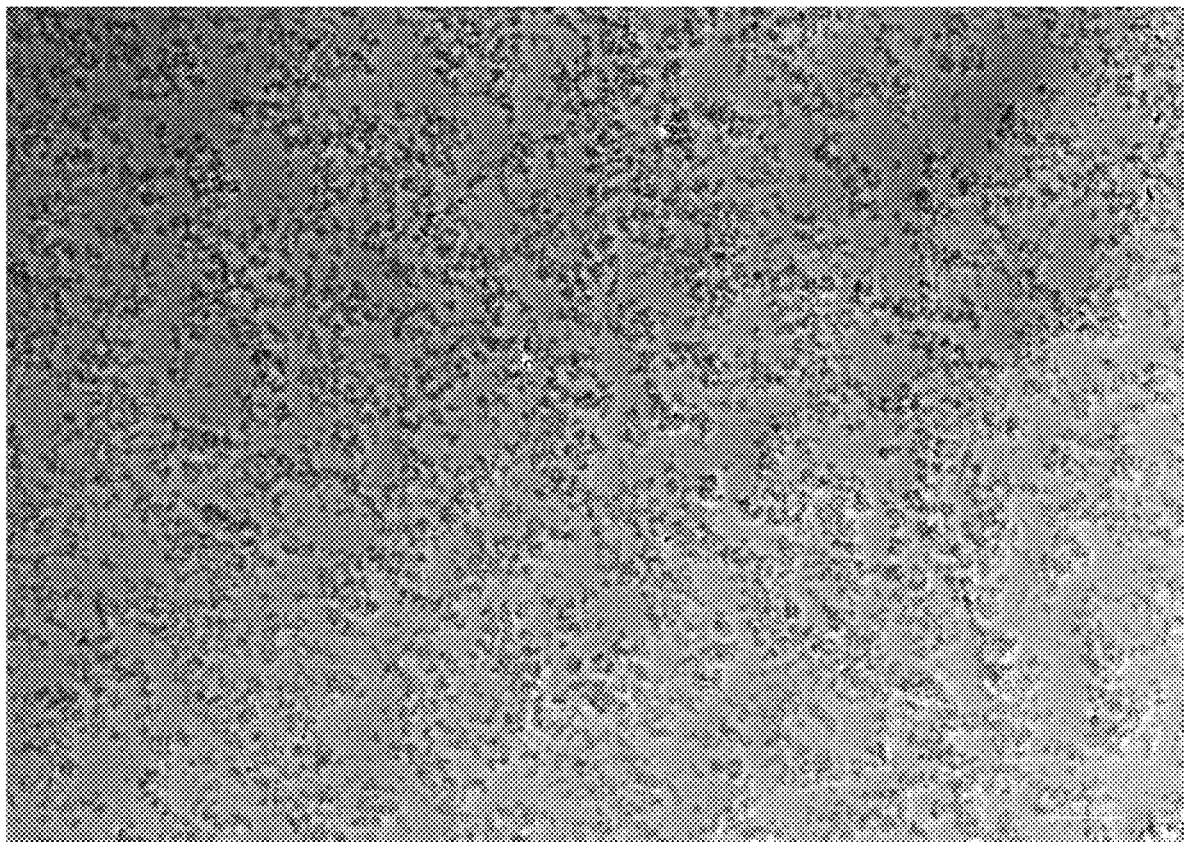

FIGS. 6A-B present microscopic images of alginate particles in a smear of a five-fold diluted supporting medium without xanthan gum (FIG. 6A) or supplemented with final concentration of 0.05% w/v xanthan gum (FIG. 6B), wherein the images were taken 30 minutes after vortexing.

As can be seen in FIGS. 6A-B, supplementation with as low as 0.05% (w/w or w/v) final concentration of xanthan gum improved particles' dispersion and prevented aggregation over time.

Example 4

Xanthan Gum Solution as Support Medium

As discussed hereinabove, it was surprisingly found that a pure xanthan gum solution (e.g., 1% w/v solution in cell media) can serve as a support medium for 3D printing, resulting in adequate accuracy and printing resolution. Xanthan gum at a concentration of about 1% or higher can be used as a transparent, easy to prepare, low-cost, temperature insensitive, non-animal-originate support media for 3D printing of biological and other materials.

As xanthan gum is a polysaccharide derived from fermentation of simple sugars by the gram-negative bacteria (*Xanthomonas campestris*), commercially available xanthan gum preparations may contain endotoxins that are known to elicit in-vivo immunogenic/pyrogenic reaction. In order to eliminate this possible adverse effect, a method for destruction of endotoxins in xanthan gum preparations has been developed without damaging the xantan's beneficial properties. To this end, concentrated xanthan gum solution was treated with sodium hydroxide (NaOH) that eliminate the pyrogenicity and adverse immunogenic activity of the endotoxins. The NaOH was then extracted from the xanthan by washing with ethanol:water solutions.

Specifically, xanthan gum was solubilized in 150 mM NaCl aqueous solution to reach a final concentration of 4% w/v. The resulting viscous solution was then sterilized by autoclaving. Thereafter, 5 M NaOH solution is added (at 1:4 v/v ratio) and mixed with the xanthan gum solution to reach a final concentration of 1 M NaOH in the mixture. After 24 hours, the mixture was transferred into a 50% (v/v, in water) ethanol solution that was 10 times larger in volume. Under these conditions, the xanthan gum gel remains stable (as an alcoholic gel—"alcogel"); but the solutes (NaOH and NaCl) diffuse and solubilized in the 50% ethanol solution that was exchanged every 24 hours. When the solution has reached a neutral pH, the xanthan gum was washed twice with 70% ethanol (v/v, in water), and twice with pure ethanol, with exchange every 24 hours. Finally, the insoluble xanthan was separated from the ethanol. Ethanol residues were then evaporated under a jet of a sterile, dry air, followed by vacuum drying at room temperature. The resulting sterile, depyrogenated pellets were stored dry for future use, or solubilized in aqueous media to be used in the preparation of particulate alginate-based printing support medium as described above, or as a "pure", non-particulate, xanthan-based support medium.

Figure 7C:
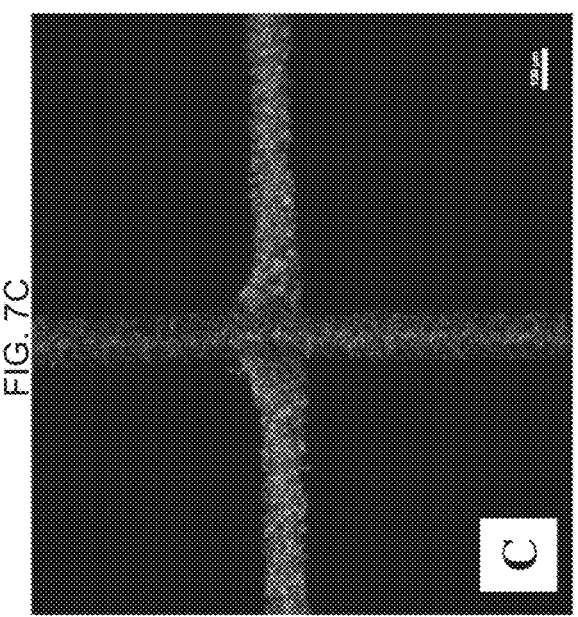
Figure 7F:
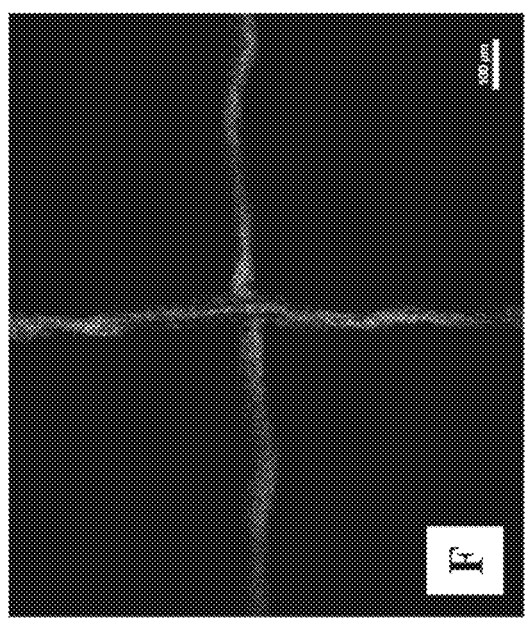
Figure 7B:
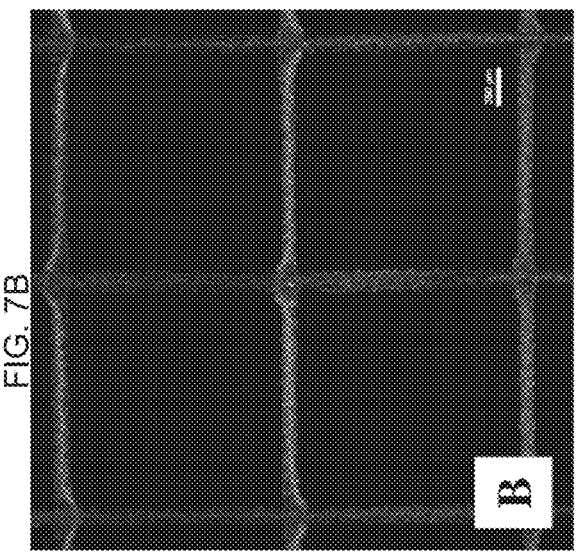
Figure 7E:
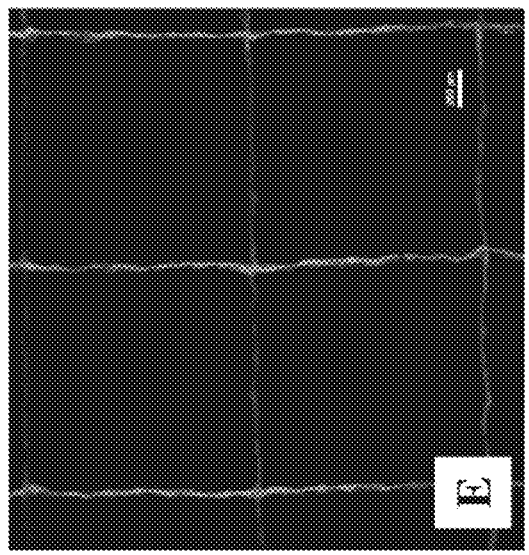
Figure 7A:
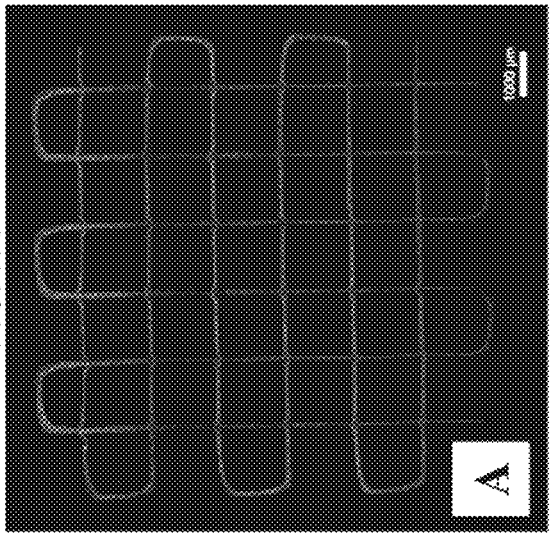
Figure 7D:
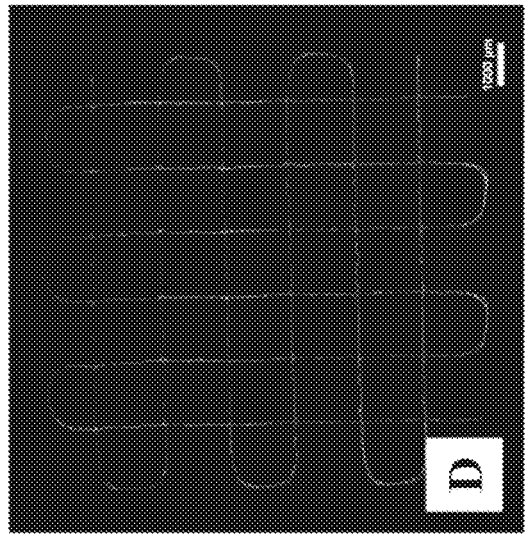

FIGS. 7A-F present microscopic images of a simple crisscross 2-layered pattern printed in two types of support media, wherein FIGS. 7A-C show the pattern as printed in a particulate alginate support medium supplemented with 0.05% w/v xanthan gum, and FIGS. 7D-F show a similar pattern printed into a support medium consisting of 1% (w/v) xanthan gum in cell growth medium.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A support composition for free-form 3D printing of inks that collapse in an uncured state, comprising a plurality of hybrid hydrogel particles, said hybrid hydrogel particles comprises calcium alginate and an aqueous-soluble polymer that is not alginate, wherein said plurality of hybrid hydrogel particles is characterized by an average size that ranges from 0.1 µM to 5 µM, and homogeneity characterized by a particle size distribution of less than 20% RSD, and wherein said plurality of hybrid hydrogel particles is substantially transparent to visible light.

2. The support composition of claim 1, wherein said aqueous-soluble polymer that is not alginate is xanthan gum.

3. The support composition of claim 2, wherein a concentration of said xanthan gum ranges 0.05%-0.5% w/w or w/v.

4. The support composition of claim 1, in a form of an aqueous slurry.

5. A selling unit comprising the support composition of claim 1.

6. The selling unit of claim 5, wherein the support composition is sterile and/or detoxified.

7. The selling unit of claim 5, wherein the support composition is ready for use without further dilution.

8. The selling unit of claim 5, wherein the support composition is in the form of a drained slurry.

9. The selling unit of claim 5, packaged in a packaging material and identified in print on or in said packaging material, for use as a support composition for free-form 3D printing process of inks that collapse in an uncured state.

10. A process of preparing the support composition of claim 1, comprising:
pulverizing a hybrid hydrogel to thereby obtain hybrid hydrogel particles; and
washing said hybrid hydrogel particles, thereby obtaining the support composition,
wherein said hybrid hydrogel comprises calcium ions, alginate and an aqueous-soluble polymer that is not alginate.

11. The process of claim 10, further comprising, prior to said pulverizing, co-jellifying alginate and said aqueous-soluble polymer that is not alginate using a source of calcium ions, thereby obtaining said hybrid hydrogel.

12. The process of claim 10, further comprising, prior to said pulverizing, jellifying alginate using a source of calcium ions to thereby obtain an alginate hydrogel, and thereafter contacting, during and/or subsequent to said pulverizing, said alginate hydrogel with an aqueous-soluble polymer that is not alginate, thereby obtaining said hybrid hydrogel particles.

13. The process of claim 11, wherein said source of calcium ions is an insoluble calcium salt.

14. The process of claim 13, wherein said jellifying is effected in the presence of an acidifying agent.

15. The process of claim 14, wherein said acidifying agent is glucono delta-lactone (GDL).

16. The process of claim 10, further comprising, subsequent to said washing, adding an aqueous-soluble polymer that is not alginate to said hydrogel-based particulate support medium.

17. The process of claim 16, wherein said adding comprises contacting the hydrogel-based particulate support medium with aqueous solution of said aqueous-soluble polymer that is not alginate at a final concentration of 0.05%-0.5% w/w or w/v.

18. The process of claim 17, further comprising, subsequent to said contacting, incubating said hybrid hydrogel particles in said aqueous solution of said aqueous-soluble polymer that is not alginate for a time period of at least 1 minute.

19. The process of claim 10, wherein said aqueous-soluble polymer that is not alginate is xanthan gum.

20. A 3D printing process, comprising:
providing a 3D printing apparatus;
providing the support composition of claim 1; and
effecting the printing process in said support composition.

* * * * *